United States Patent [19]  
Zarchy

[11] 4,406,154  
[45] Sep. 27, 1983

[54] LOW LEVEL ALKALI METAL DETECTION IN COMBUSTION GAS STREAMS

[75] Inventor: Andrew S. Zarchy, Ballston Lake, N.Y.

[73] Assignee: General Electric Company, Schenectady, N.Y.

[21] Appl. No.: 350,939

[22] Filed: Feb. 22, 1982

[51] Int. Cl.³ .............................................. G01N 27/62
[52] U.S. Cl. ........................................ 73/23; 324/468
[58] Field of Search ................... 73/23, 27 R; 324/468

[56] References Cited

U.S. PATENT DOCUMENTS 2,795,716 6/1957 Roberts ................................ 324/468
4,205,249 5/1980 Davis ................................... 324/468
4,282,741 8/1981 Zarchy .................................... 73/23

Primary Examiner—Stephen A. Kreitman
Attorney, Agent, or Firm—Lawrence D. Cutter; James C. Davis, Jr.; Marvin Snyder

[57] ABSTRACT

Alkali metal detectors previously employed in coal gasification systems are not suitable for use in combustion gas streams because of the high temperatures involved. In the present invention, alkali metal detector elements are mounted on a heat resistant flange including at least one shielded electrical ceramic feedthrough. This flange is cooled to ensure the nonconductivity of the ceramic insulation.

10 Claims, 2 Drawing Figures

LOW LEVEL ALKALI METAL DETECTION IN COMBUSTION GAS STREAMS

BACKGROUND OF THE DISCLOSURE

This invention relates to alkali metal detectors for detecting such metals in gas streams, and more particularly relates to the detection of alkali metals in combustion gas streams such as from pressurized fluidized beds.

In U.S. Pat. No. 4,282,741, issued Aug. 11, 1981 in the name of the present inventor, there is disclosed a device and method for detecting alkali metals. The teachings of this patent are directed to the use of such alkali metal detectors in coal gasification systems. In such systems the product gas from the gasifier is at a relatively low temprature, approximately 300° F. However, these gases may contain alkali metals. These metals are generally considered to be undesirable contaminants whose presence is undesired because of the corrosive and other detrimental effects that these metals have in those cases in which the product gas is used in conjunction with a conventional gas turbine. Accordingly, it is desirable to have a device and method for detecting the presence of alkali metals in such product gas streams even if the alkali metal contaminants are present only in trace amounts.

Even though the device illustrated in the aforementioned patent to Zarchy is extremely useful in the detection of alkali metals in effluent gas streams from coal gasification systems, the apparatus disclosed therein does not function at the high temperature conditions encountered in pressurized fluidized bed systems. The pressurized fluidized bed combined cycle system is an advanced power generation system that offers many advantages over current technology. In addition to the advantage of using relatively abundant coal rather than oil, the pressurized fluidized bed cycle power plant exhibits lower installation and lower operating costs than many generating plant designs. Additionally, this overall systems exhibits the ability to meet or exceed current air quality standards. It is known, though, that the effluent from a pressurized fluidized bed combustor contains undesirable levels of particulate matter containing high levels of alkali compounds. Fairly conventional techniques may be used to measure and quantify the particulate content of the effluent stream from such beds. Hence, with respect to this process contaminant, it is relatively easy to quantify, measure and evaluate various product gas cleanup systems. However, prior to the development of the instant apparatus, quantification of alkali metal vapor concentrations in such systems were not possible to obtain. A significant reason for the lack of this quantification ability is the significantly high temperature in the product gas from a pressurized fluidized bed. Such gases typically exhibit a temperature between approximately 1,800° F. and approximately 2,000° F. At such temperatures, the only practical material for providing electrical insulation for electrical feed-through connections are ceramic materials. However, even these materials, at these temperatures, exhibit conductivities which are sufficiently high to prevent accurate readings. It is recalled from the aforementioned patent to the instant inventor, which is hereby incorporated herein by reference, that the current levels of interest lie in the nanoampere range. At these extremely low current levels, even ceramic feed-through insulating materials are, without more, incapable of providing the high degree of electrical isolation required. The low levels of current found in such detector systems are a direct consequence of the fact that alkali metal concentrations extending all the way down to accuracies of a part per billion are required for proper monitoring and control of alkali metal concentrations in the product gas from the fluidized bed. It should furthermore be pointed out that in the effluent gas from pressurized fluidized beds the alkali metals are present mostly in the vapor phase rather than in the particulate form. This is a direct consequence of the high temperatures involved and does provided one advantage in that it permits in situ measurement of the alkali metal concentration in the present invention. Accordingly, since the detector can be mounted in situ, the readings are uncomplicated by sampling errors.

SUMMARY OF THE INVENTION

In accordance with a preferred embodiment of the present invention, a device for detecting the presence of one or more alkali metals in a flowing hot gas comprises a generally straight metaliferrous filament exhibiting a work function of at least 5.3 electron volts. Surrounding the filament and generally disposed in a coaxial realtionship with the filament, there is disposed an electrically conductive ion collector with apertures for the passage of hot gas through the collector. Means for applying a high voltage direct current potential difference between collector and the filament are provided. A heat resistant support flange having insulated electrical feed-through support rods disposed through it supports and insulates the filament and the collector. At least the feed-through support for the collector employs a coaxial ceramic insulator. Lastly, there is provided means for cooling the ceramic material.

Because of the high temperatures of the hot gases contemplated for use in the present invention (1,500° F. to 2,500° F.), it is not necessary to directly heat the filament, as was done in U.S. Pat. No. 4,282,741, discussed above. However, for combustion gas temperatures below approximately 1,800° F. some filament heating may be provided to increase the signal to noise ratio of the detector. In the present invention, the hot gases themselves are generally sufficient to ensure that alkali metal constituents are in the vapor phase and capable of being ionized at the metaliferrous filament. Ions formed in this region are urged toward the collector where neutralization of the ions occurs resulting in a small current through the collector. Because the current is so small (for example, $10^{-10}$ amperes) highly insulative feed-throughs are necessary. In the present invention, the electrical conductivity of the ceramic feed-through insulation, particularly that supporting the collector, is insured by providing means for cooling the ceramic material. This cooling ensures a low conductivity for the ceramic even under these extreme temperature conditions. This cooling is provided, for example, by means of fluid conduits within the flange, Furthermore, the collector assembly is preferably supported by means of a shielded feed-through to further prevent erroneous or spurious signals.

Accordingly, it is an object of the present invention to provide a device for detecting the presence of one or more alkali metals present in even trace amounts in flowing hot gas streams exhibiting temperatures of between approximately 1,500° F. to 2,500° F.

It is a further object of the present invention to provide an alkali metal detector for in situ measurement of gases from a pressurized fluidized bed and/or from gas scrubber systems fed by product gases from such beds.

It is also an object of the present invention to provide an alkali metal detector to prevent damage to gas turbine systems as a result of alkali metal contamination.

DESCRIPTION OF THE FIGURES

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

FIG. 2 is a cross-sectional side elevation view more particularly illustrating a detailed cross section showing the electrical isolation for the collector feed-through.

DETAILED DESCRIPTION OF THE INVENTION

Figure 1:
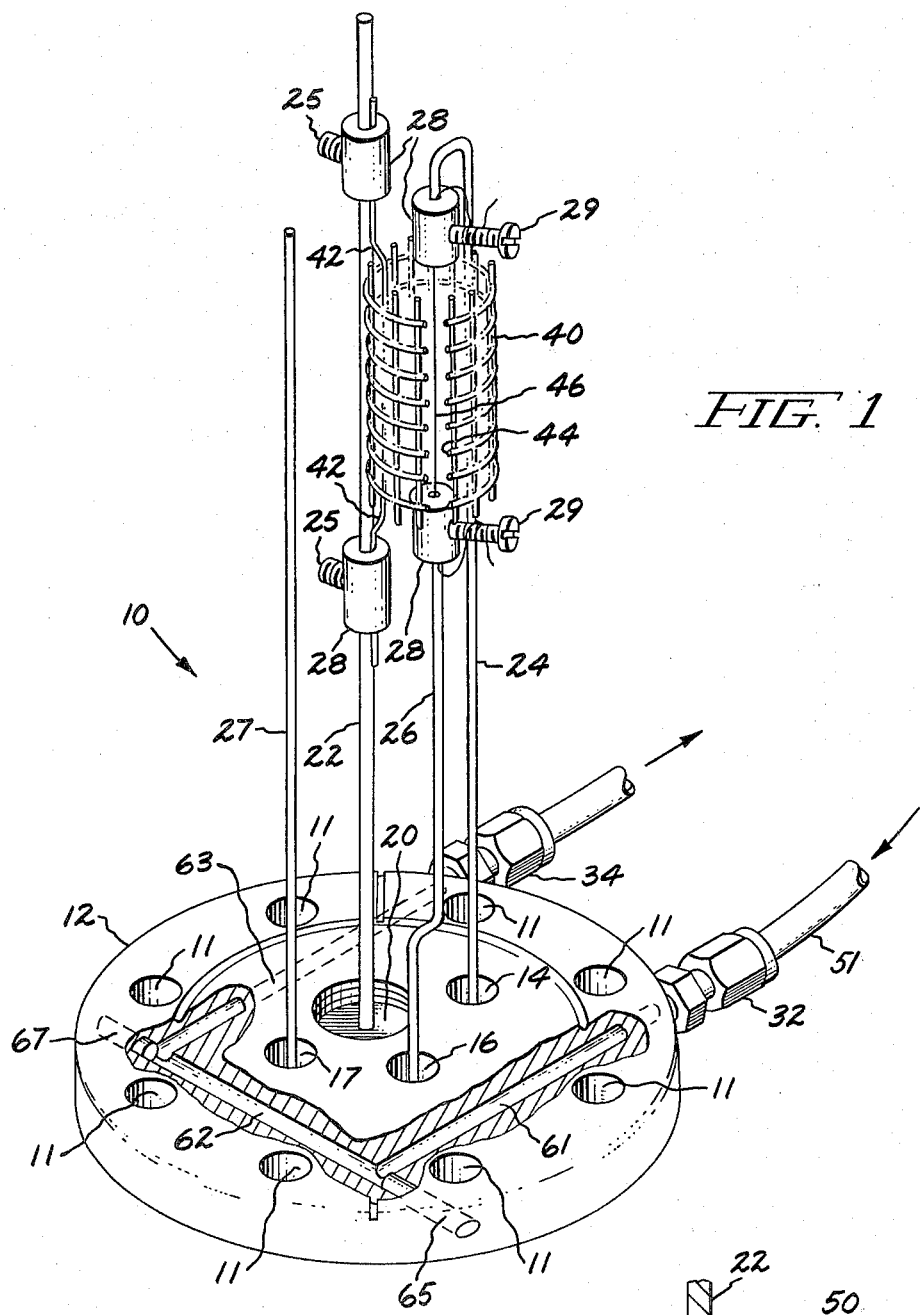
FIG. 1 is an isometric, partially sectioned view illustrating a preferred embodiment of the present invention.

FIG. 1 illustrates a preferred embodiment of the present invention in which heat resistant flange 12 acts as the supporting member for metaliferrous filament 46 and ion collector 40. By means of mounting holes 11, flange 12 may be employed to dispose and hold the entire assembly within the effluent gas flow from the pressurized fluidized bed. No separate sampling conduits need be provided. The present invention provides for in situ measurement.

The two principal electrically active elements of the present invention are the ion collector basket 40, preferably comprising a stainless steel mesh. The mesh is formed into a cylindrical shape on an appropriate mandrel and cut to size. During the cutting operation, one or more wires in the mesh, such as wire 42, are left uncut so as to provide a means for mounting basket 40 on support rod 22. This may be accomplished as shown by disposing basket wire 42 through collar 28 which is affixed to the support rod 22 by means of set screw 25. The collars, rod and set screws preferably comprise materials such as stainless steel because of the high temperature and caustic nature of the contemplated environment. Basket 40 also typically includes a gap 44 resulting from the manner in which it is typically formed. However, this gap provides a convenient means for inserting and centrally disposing the other principal electrically active element, namely the metaliferrous filament 46. This filament preferably comprises a material such as platinum, tungsten, rehenium, paladium and the alloys and oxides thereof. The most important characteristic of the filament being that it exhibits a work function of at least 5.3 electron volts. Additionally, it should also comprise a material which is not readily degraded in the proposed working environment. Filament 46 is mounted between electrically conductive supporting rods 24 and 26. Filament 46 is disposed through collars 28 as shown, which are affixed to electrically conducting supporting rods 24 and 26 by means of screws 29. Again, the screws, collars and supporting rods preferably comprise stainless steel or other high temperature corrosion-resistant conductive material. Because of the location of the present invention in the combustion gas stream, it is also convenient to provide optional thermocouple 27 mounted in feed-through 17.

While, in the present invention, it is not necessary to heat filament 46 during normal operation of the invention, it is nonetheless preferable that means be provided for preheating the filament to a temperature of approximately 1,100° C. for the purpose of driving out and removal of any alkali metal contaminants which might be present in or on the filament. For this reason, some means for heating the filament is preferred. In particular, the preferred method shown in that of electrically resistively heating the filament by applying a low voltage current through support rods 24 and 26, in a similar fashion to that shown in the previously-discussed Zarchy patent.

Several significant aspects of the present invention are associated with flange 12. In particular, flange 12 is provided with cooling conduits 61, 62 and 63 through which a cooling fluid, such as water, may be circulated for the purpose of maintaining the ceramic feed-through insulators employed at a sufficiently low level of electrical conductivity. In particular, conduit 51 receives cooling fluid through coupling 32 and the fluid circulates through conduit 62 and thence to conduit 63 from which it exits through fluid coupling 34. Of course, the flow directions could be reversed with no significant consequence. There are many ways in which such conduits may be employed in flange 12 which typically comprises a metal such as steel. In particular, conduit 61 and 63 may be drilled straight in with conduit 62 being drilled across the flange as shown, after which plugs 65 and 67 may be inserted and welded into place. Such a construction procedure provides the desired U-shaped conduit path. Fluid flowing through these conduits cools the flange and ceramic feed-through insulation material employed in fed-throughs 14, 16, 17 and particularly 20. It is the feed-through connection in feed-through 20 which is of primary importance in the particular application since the significant quantity of interest herein is the current through the collector circuit. Feed-through 20 is preferably a triaxial ceramic feed-through insulation assembly, such as that more particularly illustrated in FIG. 2, discussed below.

Figure 2:
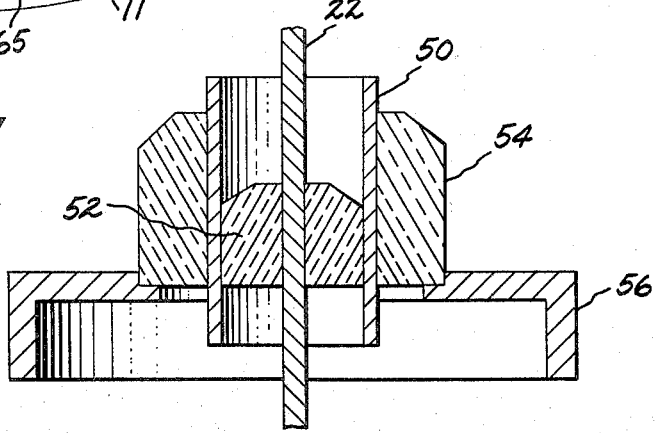

FIG. 2 is a cross-sectional side elevation view illustrating the detailed construction of the triaxial feed-through insulation apparatus 20 shown in FIG. 1. In this insulation configuration, support rod 22 is disposed through inner ceramic insulator 52. Surrounding insulator 52 is metal sleeve 50 operating to further shield conductive rod 22 from extraneous electrical effects. Ceramic sleeve 54 in turn surrounds the sleeve 50. Ceramic insulator 54 is in turn mounted on feed-through flange 56 which is rigidly affixed to the underside of flange 12 (not visible in FIG. 1). It is in particular insulators 52 and 54 which the cooling conduits serve to cool. Because of the high temperatures employed, these insulators can exhibit increased levels of conductivity thereby interferring with proper current signals through rod 22. Cooling of these ceramic insulators prevents this condition.

From the above it is appreciated that the present invention provides an accurate and reliable instrument for detecting the presence and quantity of alkali metal contaminants in the effluent product gas from a pressurized fluidized bed. Morover, because of the temperatures employed, the present invention is operable without supplying low voltage heating current filament. On the other hand, because the present invention is compatible with the high temperatures associated with pressurized fluidized beds, measurement of alkali metal contaminant concentrations may be made in situ more accurately than previously. This is significant for the proper development and operation of gas scrubbers employed in such systems.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

The invention claimed is:

1. A device for detecting the presence of one or more alkali metals present in trace amounts in a flowing hot gas, comprising:
    a metaliferrous filament having a work function of at least 5.3 electron volts;
    an electrically conductive ion collector disposed at a substantially constant distance from said filament so as to define an ionization collection region therebetween, said collector having a plurality of apertures therein for the passage of said gases;
    means for applying a high voltage, direct current potential difference between said collector and said filament, whereby alkali metal ions formed at said filament are urged toward said collector where neutralization of said ions occurs, resulting in current through said collector;
    a heat resistant support flange having insulated electrical feed-through support rods disposed therethrough for supporting said collector and said filament, said feed-through insulation, at least for said collector support rod, comprising ceramic material; and
    means for cooling said ceramic material.

2. The device of claim 1 in which said rod supporting said collector is disposed through a shielded feed-through in said flange.

3. The device of claim 2 in which said shield feed-through comprises a pair of ceramic plugs between which is coaxially disposed an electrically conductive sleeve shield.

4. The device of claim 1 in which said filament is selected from the group consisting of platinum, tungsten, rhenium, paladium, and the oxides and alloys thereof.

5. The device of claim 1 in which said means for cooling comprises at least one fluid conduit within said flange together with means for circulating cooling fluid therethrough.

6. The apparatus of claim 1 further including an insulated feed-through in said flange and a thermocouple sensor disposed therethrough.

7. The device of claim 1 further including means for removing alkali metal contaminants from said filament.

8. The device of claim 7 in which said alkali removing means comprises means to resistively heat said filament.

9. The device of claim 1 in which said ion collector comprises a cylindrically shaped screen at least partially surrounding said filament and disposed in a coaxial relationship therewith.

10. The device of claim 1 in which said filament comprises a generally straight metaliferrous conductor disposed at a fixed distance from said ion collector which comprises a planar screen.

* * * * *